(12) United States Patent
Kojima et al.

(10) Patent No.: US 9,708,260 B2
(45) Date of Patent: Jul. 18, 2017

(54) METHOD FOR PRODUCING META-XYLYLENEDIAMINES AND METHOD FOR PRODUCING BISAMIDE COMPOUND

(71) Applicant: MITSUI CHEMICALS, INC., Minato-ku, Tokyo (JP)

(72) Inventors: Kouya Kojima, Urayasu (JP); Hidetaka Tsukada, Omuta (JP); Mamoru Takashina, Tallahassee, FL (US); Chitoshi Shimakawa, Arao (JP); Naoyuki Kakinuma, Omuta (JP)

(73) Assignee: MITSUI CHEMICALS INC., Tokyo (JP)

( * ) Notice: Subject to any disclaimer, the term of this patent is extended or adjusted under 35 U.S.C. 154(b) by 0 days.

(21) Appl. No.: 14/903,262

(22) PCT Filed: Aug. 11, 2014

(86) PCT No.: PCT/JP2014/071246
§ 371 (c)(1),
(2) Date: Jan. 6, 2016

(87) PCT Pub. No.: WO2015/025774
PCT Pub. Date: Feb. 26, 2015

(65) Prior Publication Data
US 2016/0185722 A1    Jun. 30, 2016

(30) Foreign Application Priority Data

Aug. 23, 2013  (JP) .................................. 2013-173458

(51) Int. Cl.
*C07C 209/62* (2006.01)
*C07D 209/48* (2006.01)

(52) U.S. Cl.
CPC .......... *C07D 209/48* (2013.01); *C07C 209/62* (2013.01)

(58) Field of Classification Search
CPC .... C07C 209/62; C07C 211/27; C07D 209/48
See application file for complete search history.

(56) References Cited

U.S. PATENT DOCUMENTS

2002/0038054 A1   3/2002   Nakamura et al.
2009/0281325 A1   11/2009  Takano et al.

FOREIGN PATENT DOCUMENTS

| JP | 2002-105035 A | 4/2002 |
| JP | 2007-186504 A | 7/2007 |
| JP | 2011-162697 A | 8/2011 |

OTHER PUBLICATIONS

Chernyavskaya et al.: "Synthesis of Aliphatic-Aromatic Diamines Containing Halogen Atoms in Their Benzene Rings", Ikrainskii Khimicheskii Zhurnal, vol. 34, pp. 941-943, 1968 (8 pages including partial English translation).
Liu et al.: "The Synthesis of Sulfonated Phthalimidomethyl Copper Phthalocyanines", Chemical World, the 6$^{th}$ phase, pp. 302-305, 2003 (13 pages including partial English translation).
H. Fan: "Study of Dehalogenation by Hydrogenation of Benzene Halide", Science Press, pp. 377-381, 2001 (4 pages with English Abstract contained in the press).
PCT International Preliminary Report on Patentability (IPRP) and Written Opinion mailed on Dec. 23, 2015, in corresponding International Application No. PCT/JP2014/071246 (12 pages).
International Search Report (PCT/ISA/210) issued on Nov. 4, 2014, by the Japanese Patent Office as the International Searching Authority for International Application No. PCT/JP2014/071246.
Written Opinion (PCT/ISA/237) issued on Nov. 4, 2014, by the Japanese Patent Office as the International Searching Authority for International Application No. PCT/JP2014/071246.
Barwell, N.P. et al., "Substituent Effects in Synthetic Lectins—Exploring the Role of CH-π Interactions in Carbohydrate Recognition", The Journal of Organic Chemistry, vol. 76, Scheme 1, Compound 11-12, pp. 6548-6557 (2011).
Helvetica Chimica Acta., Compound 1 , vol. XXX, pp. 1845-1852 (1947).
Murai, M. et al., "Gold(I)-Catalyzed Asymmetric Induction of Planar Chirality by Intramolecular Nucleophilic Addition to Chromium-Complexed Alkynylarenes: Asymmetric Synthesis of Planar Chiral (1H-Isochromene and 1,2-Dihydroisoquinoline)Chromium Complexes", The Journal of Organic Chemistry, vol. 78, Scheme 2, Compound 9-10, pp. 10986-10995, Oct. 2, 2013.
Bensel et al.: "Straightforward Synthesis of N-Protected Benzylic Amines by Carbamoalkylation of Aromatic Compounds," Tetrahedron Letters, vol. 40, No. 5, pp. 879-882, 1999.
Plenio et al.: "The Coordination Chemistry of Fluorocarbons: Difluoro-m-cyclophane-Based Fluorocryptands and Their Group I and II Metal Ion Complexes," Inorganic Chemistry, vol. 36, No. 25, pp. 5722-5729, 1997.

*Primary Examiner* — Valerie Rodriguez-Garcia
(74) *Attorney, Agent, or Firm* — Buchanan, Ingersoll & Rooney PC

(57) ABSTRACT

A method for producing meta-xylylenediamines includes a reaction step in which monohalogenated benzenes, formaldehydes, and an amide compound having a primary amide group or a secondary amide group are allowed to react in the presence of an acidic liquid, a dehalogenation step in which the halogen atom derived from the monohalogenated benzenes is replaced with a hydrogen atom, and a deprotection step in which the primary amide group or the secondary amide group derived from the amide compound is converted to an amino group. In the reaction step, the acidic liquid contains inorganic acid, the equivalent ratio of the hydrogen atom of the inorganic acid relative to the monohalogenated benzenes is more than 16; the acidic liquid has an inorganic acid concentration of more than 80 mass %; and the reaction temperature is more than 40° C.

7 Claims, No Drawings

METHOD FOR PRODUCING META-XYLYLENEDIAMINES AND METHOD FOR PRODUCING BISAMIDE COMPOUND

TECHNICAL FIELD

The present invention relates to a method for producing meta-xylylenediamines and a method for producing a bisamide compound.

BACKGROUND ART

Conventionally, metaxylylenediamines are well-known as a polyamide material used for, for example, fiber and films. Metaxylylenediisocyanates derived from such metaxylylenediamines are useful for, a material of polyurethane used for, for example, paints, adhesives, and plastic lenses.

Patent Document 1 has proposed the following, for example, as a method for producing metaxylylenediamines: metaxylene is subjected to ammoxidation using a fluid catalyst composed of, for example, vanadium to produce isophtalonitrile, and the isophtalonitrile is hydrogenated in the presence of, for example, a nickel catalyst.

CITATION LIST

Patent Document

Patent Document 1: Japanese Unexamined Patent Publication No. 2002-105035

SUMMARY OF THE INVENTION

Problem to be Solved by the Invention

However, when metaxylylenediamine is produced by the method described in Patent Document 1, metaxylene has to be subjected to ammoxidation at a very high temperature of 420° C. to produce isophtalonitrile, and thereafter, the produced isophtalonitrile has to be hydrogenated at a very high pressure of 12 MPa (e.g., Patent Document 1 (Example 1)).

That is, in the method described in Patent Document 1, each of the steps is performed under high temperature and/or high pressure conditions. Therefore, improvements in facilities and safety are desired.

The present invention is achieved in view of such disadvantages, and its purpose is to provide a meta-xylylenediamines producing method which does not require high temperature and high pressure (special equipment), and which is excellent in terms of facilities, safety, and economy.

Means for Solving the Problem

A method for producing meta-xylylenediamine of the present invention includes a reaction step in which monohalogenated benzene, formaldehydes, and an amide compound having a primary amide group or a secondary amide group are allowed to react in the presence of an acidic liquid, a dehalogenation step in which the halogen atom derived from the monohalogenated benzene is replaced with a hydrogen atom, and a deprotection step in which the primary amide group or the secondary amide group derived from the amide compound is converted to an amino group, wherein in the reaction step, the acidic liquid contains inorganic acid, the equivalent ratio of the hydrogen atom of the inorganic acid relative to the monohalogenated benzenes is more than 16, the acidic liquid has an inorganic acid concentration of more than 80 mass %, and the reaction temperature is more than 40° C.

It is preferable that the amide compound is phthalimide represented by general formula (1) below:

General Formula (1):

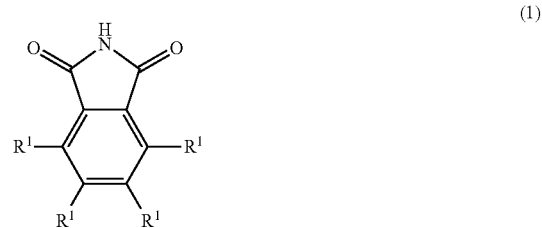

(in general formula (1), $R^1$ represents a hydrogen atom, a halogen atom, or an alkyl group, and $R^1$ may be the same or different from each other).

It is preferable that the method for producing meta-xylylenediamine further includes a collection step in which the phthalic acid eliminated in the deprotection step is collected, and then the collected phthalic acid, ammonia and/or urea are allowed to react, thereby preparing the phthalimide.

It is preferable that the inorganic acid is sulfuric acid.

It is preferable that the monohalogenated benzene is monochlorobenzene.

It is preferable that the equivalent ratio of the hydrogen atom of the inorganic acid relative to the monohalogenated benzene is 18 or more, the acidic liquid has an inorganic acid concentration of 88 mass % or more, and the reaction temperature is 50° C. or more.

A method for producing a bisamide compound of the present invention includes a reaction step in which monohalogenated benzene, formaldehydes, and an amide compound having a primary amide group or a secondary amide group are allowed to react in the presence of an acidic liquid, wherein in the reaction step, the acidic liquid contains inorganic acid, the equivalent ratio of the hydrogen atom of the inorganic acid relative to the monohalogenated benzene is more than 16, the acidic liquid has an inorganic acid concentration of more than 80 mass %, and the reaction temperature is more than 40° C.

Effect of the Invention

In the method for producing meta-xylylenediamines and the method for producing a bisamide compound of the present invention, monohalogenated benzenes, formaldehydes, and an amide compound are allowed to react at a reaction temperature of more than 40° C. in the presence of an acidic liquid of the above-described conditions. In this manner, a bisamide compound such as, for example, bisphthalimide compounds represented by Chemical Formula (2) and Chemical Formula (3) below can be produced.

Chemical Formula (2):

(2)

Chemical Formula (3):

(3)

Such a bisamide compound can be derived into meta-xylylenediamines by the deprotection step and the dehalogenation step.

Therefore, the method for producing meta-xylylenediamines and the method for producing a bisamide compound of the present invention are excellent in terms of facility, safety, and economy, can produce a bisamide compound and also meta-xylylenediamines safely, at low costs, and with a high yield. Therefore, the present invention can be suitably used as an industrial production method of meta-xylylenediamines.

DESCRIPTION OF EMBODIMENTS

The method for producing meta-xylylenediamines of the present invention includes a reaction step, a dehalogenation step, and a deprotection step, and preferably, further includes a collection step. In the following, each step is described in detail.

[Reaction Step]

In the reaction step, monohalogenated benzenes, formaldehydes, and an amide compound having a primary amide group or a secondary amide group are allowed to react in the presence of an acidic liquid to produce a bisamide compound.

The monohalogenated benzenes are aromatic compounds in which one of the hydrogen atoms bonded to the benzene ring is replaced with a halogen atom, and examples thereof include monohalogenated benzenes represented by general formula (4) below and monohalogenated benzenes represented by general formula (5) below.

General Formula (4):

(4)

(in general formula (4), X represents a halogen atom. $R^2$ represents a hydrogen atom, an alkyl group, an amino group, a hydroxyl group, or an alkoxy group. $R^2$ may be the same or different from each other.)

General Formula (5):

(5)

(in general formula (5), X and $R^2$ are the same as X and $R^2$ of the above-described general formula (4))

In each of general formula (4) and general formula (5), examples of the halogen atom represented by X include a fluorine atom, a chlorine atom, a bromine atom, and an iodine atom. Of these halogen atoms, in view of material costs, preferably, a chlorine atom, a bromine atom, or an iodine atom is used, and even more preferably, a chlorine atom is used.

In each of general formula (4) and general formula (5), examples of the alkyl group represented by $R^2$ include a straight chain alkyl group having 1 to 12 carbon atoms (e.g., methyl group, ethyl group, n-propyl group, n-butyl group, pentyl group, hexyl group, heptyl group, n-octyl group, nonyl group, decyl group, dodecyl group, etc.), and a branched alkyl group having 1 to 12 carbon atoms (e.g., isopropyl group, isobutyl group, t-butyl group, isopentyl group, isooctyl group, 2-ethylhexyl group, 2-propylpentyl group, isodecyl group, etc.).

In each of general formula (4) and general formula (5), the amino group represented by $R^2$ can be any of a primary, secondary, and tertiary amino group. Examples of the secondary and tertiary amino groups include an amino group containing, for example, the above-described alkyl group.

In each of general formula (4) and general formula (5), examples of the alkoxy group represented by $R^2$ include an alkoxy group having 1 to 12 carbon atoms (e.g., methoxy group, ethoxy group, propoxy group, butoxy group, etc.).

In each of general formula (4) and general formula (5), of the examples of $R^2$, in view of orientation of monohalogenated benzenes, preferably, a hydrogen atom is used. Furthermore, in each of general formula (4) and general formula (5), all of $R^2$ are preferably the same. In each of general formula (4) and general formula (5), when all of $R^2$ are hydrogen atoms, the monohalogenated benzenes represented by general formula (4) and general formula (5) are the same.

Of these monohalogenated benzenes, in view of material costs and orientation, preferably, monochlorobenzene is used. These examples of monohalogenated benzenes can be used singly, or can be used in combination.

Examples of formaldehydes include formaldehyde and paraformaldehyde, and in view of handleability, preferably, paraformaldehyde is used.

Paraformaldehyde is a homopolymer produced by polymerization of only formaldehyde, and is represented by general formula (6) below.

General formula (6):

$$HO(CH_2O)_nH \quad (6)$$

(in general formula (6), n represents an integer of 2 or more and 100 or less).

In general formula (6), n represents preferably 8 or more and 100 or less.

Those examples of the formaldehydes can be used singly, or can be used in combination.

Those examples of the formaldehydes are preferably prepared as an aqueous solution in view of handleability. When the formaldehydes are prepared as an aqueous solution, the concentration of the formaldehydes is, for example, 70 mass % or more, in view of reactivity, preferably 80 mass % or more, and for example, 100 mass % or less.

The mixing ratio of the formaldehydes relative to 1 mol of the monohalogenated benzenes is, for example, 1.0 mol or more, in view of the bisamide compound yield, preferably 1.2 mol or more, and for example, 10.0 mol or less, and in view of material costs, preferably 3.0 mol or less.

The mixing ratio of the formaldehydes relative to 100 parts by mass of the monohalogenated benzenes is, for example, 30 parts by mass or more, preferably 40 parts by mass or more, and for example, 70 parts by mass or less, preferably 60 parts by mass or less.

The amide compound having a primary amide group or a secondary amide group is an amide compound having an amide group having at least one N—H bond, and examples thereof include an imide compound having an imide group, an urea compound having an urea group, and a urethane compound having a urethane group.

Of these examples of the amide compound, in view of stability of the bisamide compound produced in the reaction step, preferably, an imide compound is used, and even more preferably, phthalimides represented by general formula (1) below are used.

General formula (1):

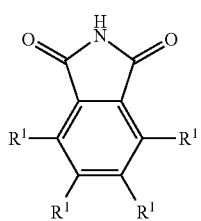

(1)

(in general formula (1), $R^1$ represents a hydrogen atom, a halogen atom, or an alkyl group, and $R^1$ may be the same or different from each other).

In general formula (1), examples of the halogen atom represented by $R^1$ include the halogen atom represented by X in general formula (4).

In general formula (1), examples of the alkyl group represented by $R^1$ include the above-described alkyl group represented by $R^2$ in general formula (4).

In general formula (1), of these examples of $R^1$, in view of reactivity, preferably, a hydrogen atom is used. Furthermore, in general formula (1), all of $R^1$ are preferably the same.

The acidic liquid is a liquid containing an inorganic acid, and used also as a reaction solvent in the reaction step. Such an acidic liquid can be composed of only an inorganic acid, or can be an aqueous solution of inorganic acid in which an inorganic acid is dissolved in water.

Examples of the inorganic acid include inorganic acids such as hydrochloric acid, sulfuric acid, nitric acid, phosphoric acid, and boric acid, and in view of the bisamide compound yield, preferably, strong acid, that is, an inorganic acid having an acid dissociation constant (pKa ($H_2O$)) of 3 or less is used. Examples of the strong inorganic acid include, to be specific, hydrochloric acid, sulfuric acid, nitric acid, and phosphoric acid, and in view of the bisamide compound yield, preferably, sulfuric acid is used. Such examples of the inorganic acid can be used singly, or can be used in combination.

When the acidic liquid is an aqueous solution of inorganic acid, the acidic liquid have an inorganic acid concentration of, in view of the bisamide compound yield, more than 80 mass %, preferably 88 mass % or more, for example, less than 100 mass %, and in view of easy preparation of the aqueous solution of inorganic acid, preferably 99 mass % or less.

Those examples of the acidic liquid can be used singly, or can be used in combination. Of these examples of the acidic liquid, preferably, an aqueous solution of sulfuric acid is used.

The mixing ratio of the acidic liquid relative to 100 parts by mass of the monohalogenated benzenes is, for example, 300 parts by mass or more, and in view of the bisamide compound yield, preferably 700 parts by mass or more, for example, 2000 parts by mass or less, and in view of costs, preferably 1100 parts by mass or less.

The mixing ratio of the inorganic acid relative to 1 mol of the monohalogenated benzenes is, for example, 3 mol or more, and in view of the bisamide compound yield, preferably 8 mol or more, and for example, 15 mol or less, and in view of costs, preferably 12 mol or less.

The equivalent ratio of the hydrogen atom (equivalent ratio in mol) in the inorganic acid relative to the monohalogenated benzenes is, in view of the bisamide compound yield, more than 16, preferably 18 or more, more preferably 20 or more, and for example, 40 or less, in view of costs, preferably 30 or less.

To allow the above-described components (monohalogenated benzenes, formaldehydes, and amide compound) to react in the presence of an acidic liquid, first, the components are dissolved or dispersed in an acidic liquid.

To dissolve or disperse the components (monohalogenated benzenes, formaldehydes, and amide compound) in an acidic liquid, for example, the formaldehydes and the amide compound are dissolved in an acidic liquid to prepare an aldehyde-amide solution, and then the aldehyde-amide solution is mixed with the monohalogenated benzenes.

The aldehyde-amide solution can be mixed with the monohalogenated benzenes by a method, without particular limitation, for example, in which one of them is dropped into the other of them, and in view of the bisamide compound yield, preferably, the monohalogenated benzenes are dropped in the aldehyde-amide solution.

The conditions for the dropping are as follows: a temperature of, for example, 0° C. or more, preferably 10° C. or more, and for example, 50° C. or less, preferably 35° C. or less, and the dropping time is, for example, 15 minutes or more, preferably 30 minutes or more, and for example, 5 hours or less, preferably 3 hours or less.

Then, the mixed solution of the aldehyde-amide solution and the monohalogenated benzenes is heated, thereby allowing the monohalogenated benzenes, formaldehydes, and amide compound to react.

The reaction temperature is, in view of the bisamide compound yield, more than 40° C., preferably 50° C. or more, more preferably more than 50° C., and in view of facility and safety, for example, 100° C. or less, preferably 90° C. or less, more preferably 80° C. or less. The reaction temperature within the above-described range is advantageous in that the reaction rate is not reduced and decomposition due to excessive heating does not easily occur.

The reaction pressure is not particularly limited, and can be any of normal pressure, increased pressure, and reduced pressure, and in view of facility and safety, preferably, the reaction pressure is normal pressure (to be specific, 90 kPa to 110 kPa).

The reaction time is, for example, 1 hour or more, preferably 3 hours or more, and for example, 10 hours or less, preferably 8 hours or less, and more preferably less than 8 hours.

In this manner, monohalogenated benzenes, formaldehydes, and an amide compound are allowed to react in the acidic liquid, thereby highly selectively producing a bisamide compound (disubstituted product).

When a bisamide compound is produced (when two amide compounds are introduced into the aromatic ring), two hydrogen atoms of the monohalogenated benzenes are replaced with the above-described amide compound. To be more specific, depending on orientation of the monohalogenated benzenes, the hydrogen atoms at positions 2 and 4 of the monohalogenated benzenes are replaced with amide compounds, thereby producing a 2,4-disubstituted product, or hydrogen atoms at positions 2 and 6 of the monohalogenated benzenes are replaced with amide compounds, thereby producing a 2,6-disubstituted product (excellent regioselectivity).

Such 2,4-disubstituted product and 2,6-disubstituted product will both take meta-form when the halogen atoms are replaced with hydrogen atoms in the dehalogenation step described later, regardless of the production ratio.

Such a bisamide compound is a disubstituted product in which two hydrogen atoms of the monohalogenated benzenes are replaced with the above-described amide compounds, and is, depending on orientation of the monohalogenated benzenes, a 2,4-disubstituted product in which hydrogen atoms at positions 2 and 4 of the monohalogenated benzenes are replaced with amide compounds, or a 2,6-disubstituted product in which hydrogen atoms at positions 2 and 6 of the monohalogenated benzenes are replaced with amide compounds.

The production ratio (mol-based) of 2,4-disubstituted product relative to 2,6-disubstituted product is, for example, 1.5 times or more, preferably 2 times or more, for example, 20 times or less, preferably 10 times or less.

The production ratio of the 2,4-disubstituted product is determined by high-performance liquid chromatography (HPLC).

To be more specific, when using monohalogenated benzenes in which all of $R^2$ in the above-described general formula (4) are hydrogen atoms for the monohalogenated benzenes and using the phthalimides represented by the above-described general formula (1) as the amide compound, the bisamide compound produced in the reaction step contains a bisphthalimide compound (2,4-disubstituted product) represented by general formula (7) below, and a bisphthalimide compound (2,6-disubstituted product) represented by general formula (8) below.

General formula (7):

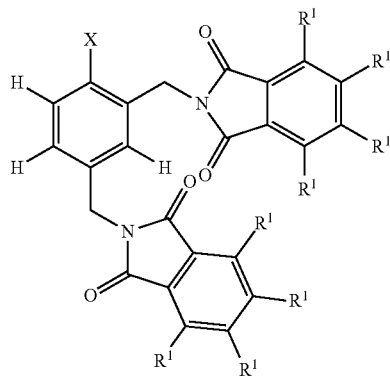

2,4-disubstituted product (in general formula (7), $R^1$ is the same as $R^1$ in the above-described general formula (1), and X is the same as X in the above-described general formula (4)).

The bisphthalimide compound represented by the above-described general formula (7) is, for example, when all of $R^1$ are hydrogen atoms and X is a chlorine atom, N,N'-(4-chloro-1,3-phenylenebismethylene) bisphthalimide (ref: the above-described Chemical Formula (2)).

General formula (8):

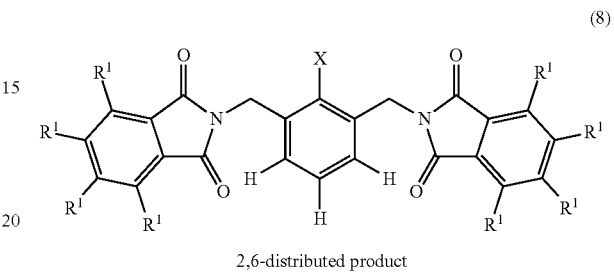

2,6-distributed product (in general formula (8), $R^1$ is the same as $R^1$ in the above-described general formula (1), and X is the same as X in the above-described general formula (4)).

The bisphthalimide compound represented by the above-described general formula (8) is, for example, when all of $R^1$ are hydrogen atoms and X is a chlorine atom, N,N'-(2-chloro-1,3-phenylenebismethylene) bisphthalimide (ref: the above-described Chemical Formula (3)).

In the reaction step, the conversion rate of the monohalogenated benzenes is, for example, 80 mol % or more, preferably 90 mol % or more, and for example, 100 mol % or less.

The yield of the bisamide compound relative to the monohalogenated benzenes is, for example, 60 mol % or more, preferably 70 mol % or more, and for example, 100 mol % or less, preferably 90 mol % or less.

The conversion rate of the monohalogenated benzenes and the yield of the bisamide compound are calculated from the integrated value of the peak determined by high-performance liquid chromatography (HPLC).

In the reaction step, in addition to the above-described bisamide compound, a monoamide compound (monosubstituted product) in which one hydrogen atom of the monohalogenated benzenes is replaced with the above-described amide compound may be produced.

In such a case, the yield of the monoamide compound relative to the monohalogenated benzenes is, for example, 1 mol % or more, for example, 20 mol % or less, preferably 15 mol % or less. The production ratio (mol-based) of the monoamide compound relative to the bisamide compound is, for example, 0.01 or more, and for example, 0.3 or less, preferably 0.2 or less.

The yield of the monoamide compound and the production ratio of the monoamide compound are calculated from the integrated value of the peak determined by high-performance liquid chromatography (HPLC).

The reaction product in the reaction step may contain, in addition to the above-described bisamide compound and the monoamide compound, impurities of the components remained in the reaction (to be specific, formaldehydes, amide compound, inorganic acid, etc.). Therefore, although the reaction product can be used as is, preferably, the reaction product is used after isolation and purification.

The reaction product can be purified by a known purification method, and examples thereof include distillation, solvent extraction, chromatography, crystallization, and recrystallization. In the purification, as necessary, separation and purification by a single purification method can be repeated, or separation and purification by two or more purification methods can be combined. Of these examples of purification methods, in view of convenience, preferably, solvent extraction is used.

To purify the reaction product by solvent extraction, for example, the reaction product is mixed with a mixed solution of water and an organic solvent, and thereafter, the water layer is removed. In this manner, at least the bisamide compound is distributed to the organic solvent (organic layer), and for example, hydrophilic impurities such as formaldehydes and inorganic acids are distributed to the water layer.

The organic solvent is not particularly limited as long as the solvent can dissolve the bisamide compound and cannot dissolve the formaldehydes and amide compound, and examples thereof include weak polar solvents such as saturated hydrocarbons (hexane, heptane, etc.), aromatic hydrocarbons (benzene, toluene, xylene, etc.), and halogenated hydrocarbons (dichloromethane, dichloroethane, carbon tetrachloride, etc.). Of these examples of the organic solvent, in view of affinity with the bisamide compound, preferably, aromatic hydrocarbons are used, and even more preferably, toluene is used. These examples of the organic solvent can be used singly, or can be used in combination of two or more.

When the reaction product contains the above-described bisamide compound and monoamide compound, the bisamide compound and the monoamide compound can be separated and purified by, for example, chromatography.

[Dehalogenation Step]

In the dehalogenation step, the halogen atom derived from the monohalogenated benzenes is replaced with a hydrogen atom in the above-described bisamide compound.

The halogen atom of the bisamide compound is replaced with a hydrogen atom by (dehalogenation method), for example, a known dehalogenation method from halogenated benzene. Of these examples of the dehalogenation method, preferably, a method in which hydrogen is supplied to the above-described bisamide compound in the presence of a catalyst is used.

Examples of the catalyst include a known hydrogenated catalyst, such as a catalyst containing metals such as Ni, Mo, Fe, Co, Cu, Pt, Pd, and Rh, and in industrial view, preferably, a palladium carbon catalyst is used. Such a catalyst can be used singly, or can be used in combination.

The catalyst is used in an amount of, relative to 100 parts by mass of the monohalogenated benzenes used in the reaction step, for example, 0.5 parts by mass or more, in view of reactivity, preferably 1 part by mass or more, and for example, 7 parts by mass or less, and in view of costs, preferably 8 parts by mass or less.

The catalyst is used in an amount relative to 100 parts by mass of the bisamide compound of, for example, 0.1 parts by mass or more, in view of reactivity, preferably 0.5 parts by mass or more, and for example, 5 parts by mass or less, in view of costs, preferably 2 parts by mass or less.

To supply hydrogen to the above-described bisamide compound in the presence of a catalyst, for example, the reactor (e.g., autoclave) is charged with the catalyst and the bisamide compound, and thereafter the air in the reactor is replaced with hydrogen.

In these examples of the dehalogenation method, as necessary, a metal salt and an organic solvent are added.

Examples of the metal salt include alkali metal carbonates (e.g., sodium carbonate, potassium carbonate, etc.), alkali metal sulfates (e.g., sodium sulfate, potassium sulfate, etc.), alkaline earth metal carbonates (e.g., magnesium carbonate, calcium carbonate, etc.), and alkaline earth metal sulfates (e.g., magnesium sulfate, calcium sulfate, etc.). Of these examples of the metal salt, preferably, alkali metal carbonates are used, even more preferably, sodium carbonate is used. These examples of the metal salt can be used singly, or can be used in combination.

The mixing ratio of the metal salt relative to 1 mol of the monohalogenated benzenes used in the reaction step is, for example, 0.1 mol or more, in view of trapping the halogen atoms to be eliminated, preferably 0.5 mol or more, for example, 3 mol or less, and in view of costs, preferably 1.5 mol or less.

For the organic solvent, for example, the above-described examples of the organic solvent is used, and preferably, aromatic hydrocarbons, even more preferably, toluene is used. These examples of the organic solvent can be used singly, or can be used in combination of two or more.

When the reaction product is purified by solvent extraction in the reaction step, the organic layer obtained in the reaction step can be used as is in the dehalogenation step without adding an organic solvent.

Then, a pressure is applied and the temperature is increased in the reactor, thereby replacing the above-described halogen atom of the bisamide compound with a hydrogen atom.

The reaction conditions in the dehalogenation are as follows: a temperature of, for example, 40° C. or more, in view of reactivity, preferably 70° C. or more, and for example, 150° C. or less, in view of facility and safety, preferably 110° C. or less; and a pressure of, for example, 0.1 MPa or more, in view of reactivity, preferably 0.2 MPa or more, and for example, 3.0 MPa or less, in view of facility and safety, preferably 1.0 MPa or less; and a duration of, for example, 1 hour or more, in view of reactivity, preferably 2 hours or more, for example, 20 hours or less, preferably 10 hours or less.

In this manner, a 1,3-amide-substituted product in which amide compounds are bonded to positions 1 and 3 is produced.

To be more specific, when the monohalogenated benzenes in which all of $R^2$ in the above-described general formula (4) are hydrogen atoms is used as the monohalogenated benzenes and the phthalimides represented by the above-described general formula (1) is used as the amide compound, a 1,3-amide-substituted product represented by general formula (9) below is produced.

General formula (9):

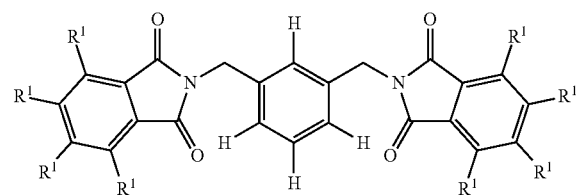

(in general formula (9), R¹ is the same as R¹ in the above-described general formula (1)).

That is, both of the bisphthalimide compound (2,4-disubstituted product) represented by the above-described general formula (7), and the bisphthalimide compound (2,6-disubstituted product) represented by the above-described general formula (8) are converted into the 1,3-amide-substituted product represented by the above-described general formula (9) by the dehalogenation step.

The yield of the 1,3-amide-substituted product relative to the bisamide compound used in the dehalogenation step is, for example, 80 mol % or more, preferably 90 mol % or more, for example, 100 mol % or less, preferably 99 mol % or less.

The yield of the 1,3-amide-substituted product is calculated from the integrated value of the peak determined by high-performance liquid chromatography (HPLC).

[Deprotection Step]

In the deprotection step, the amide group derived from the amide compound in the above-described 1,3-amide-substituted product is converted to an amino group.

The amide group is converted to the amino group by a known method without particular limitation, and preferably, the amide group can be converted to the amino group by hydrolysis.

To convert the amide group into the amino group by hydrolysis, the amide group is allowed to react with water ($H_2O$) in the presence of an acid component or a base component.

The acid component is not particularly limited, and examples thereof include inorganic acids (hydrochloric acid, sulfuric acid, nitric acid, phosphoric acid, etc.) and organic acids (sulfonic acid, acetic acid, etc.). These examples of the acid component can be used singly, or can be used in combination.

Examples of the base component include alkali metal hydroxides (sodium hydroxide, potassium hydroxide, etc.), and alkaline earth metal hydroxides (magnesium hydroxide, calcium hydroxide, etc.). These examples of the base component can be used singly, or can be used in combination.

Of these examples of the acid component and the base component, in view of reactivity, preferably, the base component is used, even more preferably, alkali metal hydroxide, and particularly preferably, sodium hydroxide is used.

The base component is prepared by, preferably, dissolved in water to be an basic aqueous solution.

In this case, the basic solution has a base component concentration of, for example, 30 mass % or more, preferably 40 mass % or more, for example, 70 mass % or less, preferably 60 mass % or less.

To convert the amide group in the above-described 1,3-amide-substituted product into the amino group, for example, the 1,3-amide-substituted product is mixed with the basic aqueous solution with stirring. In this manner, the amide group in the 1,3-amide-substituted product is allowed to react with water in the basic aqueous solution, thereby being converted to the amino group.

The reaction conditions for hydrolysis are as follows: a temperature of, for example, 60° C. or more, in view of reactivity, preferably 70° C. or more, for example, 100° C. or less, in view of safety, preferably 90° C. or less, and a duration of, for example, 0.1 hours or more, preferably 0.5 hours or more, and for example, 10 hours or less, preferably 5 hours or less.

In this manner, the amide group is converted to the amino group, thereby producing meta-xylylenediamine. To be more specific, when the monohalogenated benzenes in which all of R² in the above-described general formula (4) are hydrogen atoms is used as the monohalogenated benzenes, meta-xylylenediamine represented by Chemical Formula (10) is produced.

Chemical Formula (10):

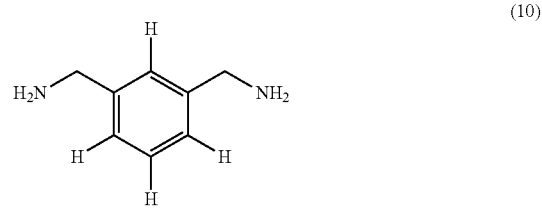

The yield of meta-xylylenediamine relative to the 1,3-amide-substituted product used in the deprotection step is, for example, 80 mol % or more, preferably 90 mol % or more, for example, 100 mol % or less, preferably 99 mol % or less.

The yield of meta-xylylenediamine is calculated from the integrated value of the peak determined by gas chromatography (GC).

In the deprotection step, along with hydrolysis of the amide group, carboxylate is eliminated. Therefore, the reaction product (crude product) in the deprotection step contains carboxylate in addition to the above-described meta-xylylenediamine.

Therefore, the crude product is preferably used after removing the carboxylate in the crude product.

The carboxylate in the crude product can be removed by any method without limitation, and for example, the above-described purification method can be used. In the purification, as necessary, separation and purification by a single purification method can be repeated, and separation and purification by two or more purification methods can be combined. Of these examples of the purification method, preferably, crystallization is used.

To remove carboxylate by crystallization from the crude product, for example, water in the reaction product is removed, and then cooled. In this manner, carboxylate is crystallized. Then, by filtering, carboxylate is separated from filtrate in which meta-xylylenediamine is dissolved.

In this embodiment, after the reaction step, the dehalogenation step is performed, and then the deprotection step is performed: however, the present invention is not limited thereto. For example, it is also possible to perform, after the reaction step, the deprotection step, and then the dehalogenation step. In this case, for example, after producing the bisphthalimide compound represented by the above-described general formula (7) in the reaction step, the amide group in the bisphthalimide compound is converted to the amino group to produce the halogenated xylylenediamine in the deprotection step, and in the dehalogenation step, halogen atom is eliminated from the halogenated xylylenediamine, thereby preparing meta-xylylenediamine.

Then, by removing the solvent from the filtrate in which meta-xylylenediamine is dissolved, meta-xylylenediamine is produced.

[Collection Step]

In the collection step, first, after converting the carboxylate produced in the deprotection step to carboxylic acid, carboxylic acid is allowed to react with urea or ammonia, thereby producing the above-described amide compound.

To convert carboxylate to carboxylic acid, for example, carboxylate is dispersed in acid to donate protons to carboxylate, thereby converting carboxylate to carboxylic acid.

For the acid, those acids given as examples of the above-described acid component can be used. Preferably, inorganic acid, even more preferably, hydrochloric acid is used. Those examples of the acid can be used singly, or can be used in combination.

The acid is prepared preferably as an acidic aqueous solution. When the acid is prepared as an aqueous solution, the acid concentration is, for example, 1 mol % or more, preferably 10 mol % or more, for example, 50 mol % or less, preferably 30 mol % or less.

Then, carboxylic acid is allowed to react with urea or ammonia.

The reaction conditions are as follows: under normal pressure, a temperature of, for example, 20° C. or more, in view of reactivity, preferably 40° C. or more, for example, 200° C. or less, and in view of safety, preferably 150° C. or less, and a duration of, for example, 30 minutes or more, preferably 2 hours or more, and for example, 50 hours or less, preferably 25 hours or less.

In this manner, the above-described amide compound, that is, amide compound used in the reaction step is produced. Therefore, the amide compound collected in the collection step can be used in the reaction step, which further improves economy.

The method for producing meta-xylylenediamines allows for production of a bisamide compound and meta-xylylenediamines safely, at low costs, and with a high yield under comparatively mild conditions relative to conventional methods. Therefore, the method for producing meta-xylylenediamines is excellent in terms of facility, safety, and economy. As a result, the method for producing meta-xylylenediamines can be suitably used as an industrial production method of meta-xylylenediamines.

The meta-xylylenediamines and its salt are suitably used as various industrial materials including resin material of, for example, polyurethane material, and for example, polyamide material.

When used as, for example, a polyurethane material, meta-xylylenediamines are derived into meta-xylylenediisocyanates by a known phosgene method or non-phosgene method.

EXAMPLES

In the following, the present invention will be described in detail with reference to Examples. However, the present invention is not limited thereto. The formulations, acidic liquids, reaction conditions, conversion rate, and yields in the reaction step for Examples and Comparative Examples are shown in Table 1.

Values such as mixing ratios in Examples can be replaced with the upper limit values or lower limit values in corresponding values in the above-described embodiments.

Furthermore, the components in each of the steps are analyzed with gas chromatography (GC) or high-performance liquid chromatography (HPLC). To be more specific, a three-point calibration curve is prepared, and based on the integrated value of the peak produced by GC or HPLC, the concentration and content of each component were calculated.

Example 1

Reaction Step

A 1 L four-neck flask equipped with a stirrer, a dropping funnel, a thermometer, and a gas discharge pipe was charged with 515.8 g (sulfuric acid: 5 mol) of a 95 mass % aqueous solution of sulfuric acid, and then further charged with 147.1 g (1 mol) of phthalimide and 33.4 g (formaldehyde: 1 mol) of a 90 mass % aqueous solution of paraformaldehyde, and the mixture was dissolved in a 95 mass % aqueous solution of sulfuric acid, thereby preparing an aldehyde-amide solution.

Then, while the temperature in the flask was kept in a temperature range of 20 to 25° C., 56.3 g (0.5 mol) of monochlorobenzene was dropped taking 1 hour (dropping speed: $8.3 \times 10^{-3}$ mol/min) to the aldehyde-amide solution. That is, the equivalent ratio (molar ratio) of the hydrogen atom of sulfuric acid relative to the monohalogenated benzenes was 20.

Thereafter, the temperature in the flask was increased to 80° C., and while the temperature was kept constant, the components were allowed to react under normal pressure. The reaction was terminated after 5 hours, and a reaction product was obtained.

The reaction product was analyzed with HPLC, and it was found that the monochlorobenzene conversion rate was 99 mol %, and the reaction product contained a bisphthalimide compound (disubstituted product) and a monophthalimide compound (monosubstituted product).

The bisphthalimide compound (disubstituted product) yield relative to monochlorobenzene was 80 mol %, and the monophthalimide compound (monosubstituted product) yield relative to monochlorobenzene was 10 mol %. That is, the bisphthalimide compound was produced in a total of 0.4 mol, and a total sum of the mass was 172.3 g.

The produced bisphthalimide compound contained only the bisphthalimide compound (2,4-disubstituted product) represented by Chemical Formula (2) below and the bisphthalimide compound (2,6-disubstituted product) represented by Chemical Formula (3) below.

Chemical Formula (2):

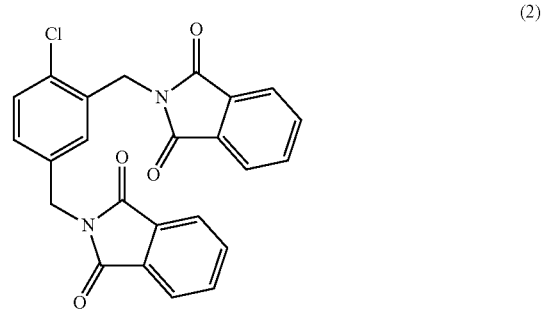 [SMILES: O=C1c2ccccc2C(=O)N1Cc1ccc(Cl)c(CN2C(=O)c3ccccc3C2=O)c1]

Chemical Formula (3):

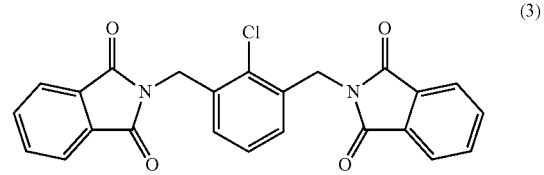 [SMILES: O=C1c2ccccc2C(=O)N1Cc1cccc(CN2C(=O)c3ccccc3C2=O)c1Cl]

The monochlorobenzene conversion rate, the bisphthalimide compound yield, and the monophthalimide compound yield were calculated from the integrated value of the peak determined by high-performance liquid chromatography (HPLC).

A 2 L flask having a drain cock and equipped with stirrer was charged with 500 g of toluene and 500 g of water, and a total amount of the reaction products was introduced by dropping, taking 15 minutes, and then the mixture was stirred.

Then, after taking out the water layer, 500 g of water was added again to the organic layer, and the mixture was stirred. This was repeated four times to wash the organic layer with water, thereby producing an organic layer in which the bisphthalimide compound and the monophthalimide compound were dissolved (bisamide solution). That is, the organic layer had a bisphthalimide compound concentration of 25.6 mass %.

[Dehalogenation Step]

Then, a 1 L autoclave equipped with a stirrer was charged with 1.5 g of palladium carbon (catalyst) and 53.0 g (0.5 mol) of sodium carbonate anhydride, and thereafter a total amount of the above-described organic layer was further introduced thereto.

Then, the gas phase portion in the autoclave was replaced with nitrogen, then replaced with hydrogen, and the hydrogen pressure was increased to 0.5 MPa. Furthermore, the temperature in the autoclave was increased to 90° C., to advance dehalogenation reaction of bisphthalimide compound. The reaction was terminated after 5 hours and cooling was performed.

The reaction solution after the cooling was filtered to separate the catalyst and the inorganic salt (sodium chloride), thereby producing a filtrate. Then, a portion of the filtrate was taken out, and the solvent (toluene) was distilled off from the filtrate, thereby producing N,N'-(1,3-phenylenebismethylene) bisphthalimide (1,3-amide-substituted product). The N,N'-(1,3-phenylenebismethylene) bisphthalimide yield relative to a total of the bisphthalimide compound of the above-described Chemical Formula (2) and represented by Chemical Formula (3) below was 98 mol %. That is, 0.39 mol of N,N'-(1,3-phenylenebismethylene) bisphthalimide was produced, and its mass was 154.6 g.

The N,N'-(1,3-phenylenebismethylene) bisphthalimide yield was calculated from the integrated value of the peak determined by high-performance liquid chromatography (HPLC).

[Deprotection Step]

A 1 L four-neck flask equipped with a stirrer, a Dean-Stark reflux pipe, a thermometer, and a gas discharge pipe was charged with a total amount of the filtrate (excluding the filtrate taken out) obtained in the dehalogenation step, then thereafter, charged with 91.7 g (1.1 mol) of a 48 mass % sodium hydroxide water, and the mixture was stirred. The temperature in the flask was increased to 80° C., and the mixture was stirred while the temperature was kept constant under normal pressure for 2 hours. Furthermore, the temperature in the flask was increased to 110 to 120° C., and water was separated and taken out by the Dean-Stark reflux pipe.

Then, after continuing the separation of water until water cannot be taken out, cooling was performed. Then, the reaction solution was filtered, and the sodium phthalate produced in the reaction was separated, thereby producing a filtrate.

The filtrate was analyzed with GC, and production of meta-xylylenediamine was confirmed. The yield of meta-xylylenediamine relative to the N,N'-(1,3-phenylenebismethylene) bisphthalimide was 97 mol %. That is, 0.38 mol of meta-xylylenediamine was produced, and its mass was 51.5 g.

[Collection Step]

159.7 g of the sodium phthalate (0.76 mol) separated in the deprotection step was dispersed to a 20 mol % hydrochloric acid in a 1 L flask, thereby converting to phthalic acid (0.76 mol). Then, urea (45.6 g) having an equal mol with phthalic acid was introduced into the flask, the temperature in the flask was increased to a temperature in a temperature range of 60° C. to 130° C., and the mixture was stirred while removing the ammonia produced to outside the flask. Phthalimide was produced in this manner. The phthalimide yield relative to sodium phthalate was 92 mol %. That is, 0.70 mol of phthalimide was collected, and its mass was 102.9 g.

Example 2

Meta-xylylenediamine was prepared in the same manner as in Example 1, except that in the reaction step, 464.6 g (sulfuric acid: 4.5 mol) of 95 mass % aqueous solution of sulfuric acid was used.

In the reaction step, the monochlorobenzene conversion rate was 99 mol %, the bisphthalimide compound (disubstituted product) yield was 81 mol %, and the monophthalimide compound (monosubstituted product) yield was 12 mol %.

Example 3

Meta-xylylenediamine was prepared in the same manner as in Example 1, except that in the reaction step, the amount of the 95 mass % aqueous solution of sulfuric acid used was changed to 464.6 g (sulfuric acid: 4.5 mol), the reaction temperature was changed to 50° C., and the reaction time was changed to 8 hours.

In the reaction step, the monochlorobenzene conversion rate was 98 mol %, the bisphthalimide compound (disubstituted product) yield was 77 mol %, and the monophthalimide compound (monosubstituted product) yield was 14 mol %.

Example 4

Meta-xylylenediamine was prepared in the same manner as in Example 1, except that in the reaction step, the concentration of the aqueous solution of sulfuric acid was changed to 98 mass % and the amount of the aqueous solution of sulfuric acid used was changed to 450.4 g (sulfuric acid: 4.5 mol).

In the reaction step, the monochlorobenzene conversion rate was 99 mol %, the bisphthalimide compound (disubstituted product) yield was 80 mol %, and the monophthalimide compound (monosubstituted product) yield was 12 mol %.

Example 5

Meta-xylylenediamine was prepared in the same manner as in Example 1, except that in the reaction step, the concentration of the aqueous solution of sulfuric acid was changed to 88 mass %, and the amount of the aqueous solution of sulfuric acid used was changed to 557.3 g (sulfuric acid: 5 mol).

In the reaction step, the monochlorobenzene conversion rate was 99 mol %, the bisphthalimide compound (disubstituted product) yield was 81 mol %, and the monophthalimide compound (monosubstituted product) yield was 8 mol %.

Comparative Example 1

The steps were performed in the same manner as in Example 1, except that in the reaction step, the amount of the aqueous solution of sulfuric acid used was changed to 413.0 g (sulfuric acid: 4 mol).

In the reaction step, the monochlorobenzene conversion rate was 90 mol %, and the monophthalimide compound (monosubstituted product) yield was 70 mol %. The bisphthalimide compound (disubstituted product) was not produced.

Comparative Example 2

The steps were performed in the same manner as in Example 1, except that in the reaction step, the amount of the 95 mass % aqueous solution of sulfuric acid used was changed to 464.6 g (sulfuric acid: 4.5 mol), the reaction temperature was changed to 40° C., and the reaction time was changed to 8 hours.

In the reaction step, the monochlorobenzene conversion rate was 92 mol %, and the monophthalimide compound (monosubstituted product) yield was 77 mol %. The bisphthalimide compound (disubstituted product) was not produced.

Comparative Example 3

The steps were performed in the same manner as in Example 1, except that in the reaction step, the concentration of the aqueous solution of sulfuric acid was changed to 80 mass %; the amount of the aqueous solution of sulfuric acid used was changed to 613.0 g (sulfuric acid: 5 mol); the reaction temperature was changed to 100° C.; and the reaction time was changed to 8 hours.

In the reaction step, the monochlorobenzene conversion rate was 88 mol %, and the monophthalimide compound (monosubstituted product) yield was 70 mol %. The bisphthalimide compound (disubstituted product) was not produced.

Comparative Example 4

The steps were performed in the same manner as in Example 1, except that in the reaction step, 33.4 g (formaldehyde: 1 mol) of 90 mass % paraformaldehyde was changed to 81.2 g (formaldehyde: 1 mol) of 37 mass % of the aqueous solution of formaldehyde, 147.1 g (1 mol) of phthalimide was changed to 85.0 g (ammonia: 1 mol) of 20 mass % ammonia water, and the reaction time was changed to 8 hours.

In the reaction step, the monochlorobenzene conversion rate was 0 mol %, and the bisphthalimide compound (disubstituted product) and the monophthalimide compound (monosubstituted product) were not produced.

Comparative Example 5

The steps were performed in the same manner as in Example 1, except that in the reaction step, 147.1 g (1 mol) of phthalimide was changed to 85.0 g (ammonia: 1 mol) of 20 mass % aqueous solution of ammonia, and the reaction time was changed to 8 hours.

In the reaction step, the monochlorobenzene conversion rate was 0 mol %, and the bisphthalimide compound (disubstituted product) and the monophthalimide compound (monosubstituted product) were not produced.

Comparative Example 6

The steps were performed in the same manner as in Example 1, except that in the reaction step, 515.8 g (sulfuric acid: 5 mol) of the 95 mass % aqueous solution of sulfuric acid was changed to 970.7 g (methanesulfonic acid: 10 mol) of a 99 mass % aqueous solution of methanesulfonic acid, and the reaction time was changed to 8 hours.

In the reaction step, the monochlorobenzene conversion rate was 2 mol %, and the bisphthalimide compound (disubstituted product) and the monophthalimide compound (monosubstituted product) were not produced.

Comparative Example 7

The steps were performed in the same manner as in Example 1, except that in the reaction step, 515.8 g (sulfuric acid: 5 mol) of the 95 mass % aqueous solution of sulfuric acid was changed to 606.6 g (acetic acid: 10 mol) of a 99 mass % aqueous solution of acetic acid, the reaction temperature was changed to 100° C., and the reaction time was changed to 8 hours.

In the reaction step, the monochlorobenzene conversion rate was 0 mol %, and the bisphthalimide compound (disubstituted product) and the monophthalimide compound (monosubstituted product) were not produced.

Comparative Example 8

The steps were performed in the same manner as in Example 1, except that in the reaction step, 56.3 g (0.5 mol) of chlorobenzene was changed to 39.1 g (0.5 mol) of benzene.

In the reaction step, the monochlorobenzene conversion rate was 99 mol %, the bisphthalimide compound (disubstituted product) yield was 20 mol %, and the monophthalimide compound (monosubstituted product) yield was 5 mol %.

Comparative Example 9

The steps were performed in the same manner as in Example 1, except that in the reaction step, the concentration of the aqueous solution of sulfuric acid was changed to 88 mass %; the amount of the aqueous solution of sulfuric acid used was changed to 557.3 g (sulfuric acid: 5 mol); the reaction temperature was changed to 30° C.; and the reaction time was changed to 8 hours.

In the reaction step, the monochlorobenzene conversion rate was 99 mol %, and the monophthalimide compound (monosubstituted product) yield was 94 mol %. The bisphthalimide compound (disubstituted product) was not produced.

Comparative Example 10

The steps were performed in the same manner as in Example 1, except that in the reaction step, the concentration of the aqueous solution of sulfuric acid was changed to 70 mass %; the amount of the aqueous solution of sulfuric acid used was changed to 1050.8 g (sulfuric acid: 7.5 mol); the reaction temperature was changed to 100° C.; and the reaction time was changed to 8 hours.

In the reaction step, the monochlorobenzene conversion rate was 99 mol %, and the monophthalimide compound (monosubstituted product) yield was 57 mol %. The bisphthalimide compound (disubstituted product) was not produced.

Comparative Example 11

The steps were performed in the same manner as in Example 1, except that in the reaction step, the concentration of the aqueous solution of sulfuric acid was changed to 48 mass %; the amount of the aqueous solution of sulfuric acid used was changed to 1021.7 g (sulfuric acid: 5 mol); the reaction temperature was changed to 100° C.; and the reaction time was changed to 8 hours.

In the reaction step, the monochlorobenzene conversion rate was 0 mol %, and the bisphthalimide compound (disubstituted product) and the monophthalimide compound (monosubstituted product) were not produced.

$NH_3$ water: 20 mol % aqueous solution of ammonia (Manufactured by Wako Pure Chemical Industries, Ltd.)
MSA: methanesulfonic acid (Manufactured by Wako Pure Chemical Industries, Ltd.)

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

With the present invention, meta-xylylenediamines can be produced under comparatively mild conditions relative to conventional methods. Therefore, in view of facilities, safety, and economy, meta-xylylenediamines can be produced more industrially and advantageously.

TABLE 1

| No. | Formulation (molar ratio) | | | | | | Acidic Liquid | | Reaction Conditions | | Conversion Rate (%) | Di-substituted Product Yield(%) | Mono-substituted Product Yield(%) |
| | CB | BZ | PFA | Formalin | PI | $NH_3$ water | Acid Type | Concentration (mass %) | Acid equivalent (H/CB) | Temperature | Time | | | |
| --- | --- | --- | --- | --- | --- | --- | --- | --- | --- | --- | --- | --- | --- | --- |
| Ex. 1 | 1.0 | — | 2.0 | — | 2.0 | — | Sulfuric acid | 95 | 20 | 80 | 5 | 99 | 80 | 10 |
| Ex. 2 | 1.0 | — | 2.0 | — | 2.0 | — | Sulfuric acid | 95 | 18 | 80 | 5 | 99 | 81 | 12 |
| Ex. 3 | 1.0 | — | 2.0 | — | 2.0 | — | Sulfuric acid | 95 | 18 | 50 | 8 | 98 | 77 | 14 |
| Ex. 4 | 1.0 | — | 2.0 | — | 2.0 | — | Sulfuric acid | 98 | 18 | 80 | 5 | 99 | 80 | 12 |
| Ex. 5 | 1.0 | — | 2.0 | — | 2.0 | — | Sulfuric acid | 88 | 20 | 80 | 5 | 99 | 81 | 8 |
| Comp. Ex. 1 | 1.0 | — | 2.0 | — | 2.0 | — | Sulfuric acid | 95 | 16 | 80 | 5 | 90 | 0 | 70 |
| Comp. Ex. 2 | 1.0 | — | 2.0 | — | 2.0 | — | Sulfuric acid | 95 | 18 | 40 | 8 | 92 | 0 | 77 |
| Comp. Ex. 3 | 1.0 | — | 2.0 | — | 2.0 | — | Sulfuric acid | 80 | 20 | 100 | 8 | 88 | 0 | 70 |
| Comp. Ex. 4 | 1.0 | — | — | 2.0 | — | 2.0 | Sulfuric acid | 95 | 20 | 80 | 8 | 0 | 0 | 0 |
| Comp. Ex. 5 | 1.0 | — | 2.0 | — | — | 2.0 | Sulfuric acid | 95 | 20 | 80 | 8 | 0 | 0 | 0 |
| Comp. Ex. 6 | 1.0 | — | 2.0 | — | 2.0 | — | MSA | 99 | 20 | 80 | 8 | 2 | 0 | 0 |
| Comp. Ex. 7 | 1.0 | — | 2.0 | — | 2.0 | — | Acetic Acid | 99 | 20 | 100 | 8 | 0 | 0 | 0 |
| Comp. Ex. 8 | — | 1.0 | 2.0 | — | 2.0 | — | Sulfuric acid | 95 | 20(H/BZ) | 80 | 5 | 99 | 20 | 5 |
| Comp. Ex. 9 | 1.0 | — | 2.0 | — | 2.0 | — | Sulfuric acid | 88 | 20 | 30 | 8 | 99 | 0 | 94 |
| Comp. Ex. 10 | 1.0 | — | 2.0 | — | 2.0 | — | Sulfuric acid | 70 | 30 | 100 | 8 | 99 | 0 | 57 |
| Comp. Ex. 11 | 1.0 | — | 2.0 | — | 2.0 | — | Sulfuric acid | 48 | 20 | 100 | 8 | 2 | 0 | 0 |

The abbreviations in Table 1 are shown below.
CB: monochlorobenzene (manufactured by Tokyo Chemical Industry Co., Ltd.)
BZ: benzene (manufactured by Wako Pure Chemical Industries, Ltd.)
PFA: paraformaldehyde (manufactured by Tokyo Chemical Industry Co., Ltd.)
Formalin: 37 mass % aqueous solution of formaldehyde (Manufactured by Wako Pure Chemical Industries, Ltd.)
PI: phthalimide (Manufactured by Wako Pure Chemical Industries, Ltd.)

The meta-xylylenediamines are used suitably for applications in polyamide, polyimide, polyurethane, polythiourethane, polyisocyanate, and a curing agent for epoxy resin for higher performance. Particularly, it is suitable for applications in polyurethane paints, adhesives, sealants, elastomers, and polythiourethane-based lenses.

The invention claimed is:
1. A method for producing meta-xylylenediamine, comprising:
a reaction step in which monohalogenated benzene, formaldehydes, and an amide compound having a primary amide group or a secondary amide group are allowed to react in the presence of an acidic liquid,
a dehalogenation step in which the halogen atom derived from the monohalogenated benzene is replaced with a hydrogen atom, and
a deprotection step in which the amide group derived from the amide compound is converted to an amino group,
wherein in the reaction step,
the acidic liquid contains inorganic acid,
the equivalent ratio of the hydrogen atom of the inorganic acid relative to the monohalogenated benzenes is more than 16,
the acidic liquid has an inorganic acid concentration of more than 80 mass %, and
the reaction temperature is more than 40° C.

2. The method for producing meta-xylylenediamine according to claim 1, wherein the amide compound is phthalimide represented by formula (1) below:
Formula (1):

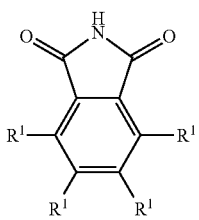

wherein, $R^1$ represents a hydrogen atom, a halogen atom, or an alkyl group, and $R^1$ may be the same or different from each other.

3. The method for producing meta-xylylenediamine according to claim 2, further comprising a collection step in which phthalic acid eliminated in the deprotection step is collected, and then the collected phthalic acid is reacted with ammonia and/or urea, thereby preparing phthalimide.

4. The method for producing meta-xylylenediamine according to claim 1, wherein the inorganic acid is sulfuric acid.

5. The method for producing meta-xylylenediamine according to claim 1, wherein the monohalogenated benzene is monochlorobenzene.

6. The method for producing meta-xylylenediamine according to claim 1, wherein
the equivalent ratio of the hydrogen atom of the inorganic acid relative to the monohalogenated benzene is 18 or more,
the acidic liquid has an inorganic acid concentration of 88 mass % or more, and
the reaction temperature is 50° C. or more.

7. A method for producing a meta-xylylenebisamide compound comprising:
a reaction step in which monohalogenated benzene, formaldehydes, and an amide compound having a primary amide group or a secondary amide group are allowed to react in the presence of an acidic liquid,
wherein in the reaction step,
the acidic liquid contains inorganic acid,
the equivalent ratio of the hydrogen atom of the inorganic acid relative to the monohalogenated benzene is more than 16,
the acidic liquid has an inorganic acid concentration of more than 80 mass %, and the reaction temperature is more than 40° C.

* * * * *